United States Patent
Bogin et al.

(10) Patent No.: US 7,264,946 B2
(45) Date of Patent: Sep. 4, 2007

(54) THERMOANAEROBACTER BROCKII ALCOHOL DEHYDROGENASE PROMOTER FOR EXPRESSION OF HETEROLOGOUS PROTEINS

(75) Inventors: Oren Bogin, Moshav Ganei Yohanan (IL); Avner Yayon, Moshav Sitria (IL); Moshe Peretz, Moshav Beit Gamliel (IL); Yigal Burstein, Rehovot (IL)

(73) Assignees: ProChon Biotech Ltd., Rehovot (IL); Yeda Research and Development Co., Ltd., Rehovot (IL)

( * ) Notice: Subject to any disclaimer, the term of this patent is extended or adjusted under 35 U.S.C. 154(b) by 500 days.

(21) Appl. No.: 10/389,821

(22) Filed: Mar. 18, 2003

(65) Prior Publication Data

US 2004/0058348 A1 Mar. 25, 2004

Related U.S. Application Data

(63) Continuation of application No. PCT/IL01/00870, filed on Sep. 16, 2001.

(30) Foreign Application Priority Data

Sep. 18, 2000 (IL) .................................. 138529

(51) Int. Cl.
 *C12N 15/00* (2006.01)
 *C12N 5/10* (2006.01)
 *C12P 21/02* (2006.01)
 *C07H 21/04* (2006.01)

(52) U.S. Cl. ............. 435/69.1; 435/320.1; 435/254.11; 435/252.3; 536/24.1

(58) Field of Classification Search ...................... None
See application file for complete search history.

(56) References Cited

U.S. PATENT DOCUMENTS 5,908,924 A * 6/1999 Burdette et al. ............ 536/23.2

OTHER PUBLICATIONS

Khlebnikov et al. Modulation of gene expression from the arabinose-inducible araBAD promoter. J Ind Microbiol Biotechnol. vol. 29, No. 1, pp. 34-37, Jul. 2002.*
GenBank Accession No. AF157307.1, publicly available Sep. 14, 1999.*
Peretz et al. Molecular cloning, nucleotide sequenceing, and expression of genes encoding alcohol dehydrogenases from the thermophile Thermoanaerobacter brockii and the mesophile Clostridium beijerinckii. Anaerobe, vol. 3, pp. 259-270, 1997.*
McDonald et al. Large-scale purification and characterization of recombinant fibroblast growth factor-saporin mitotoxin. Protein Expression and Purification, vol. 8, pp. 97-108, 1996.*
Burdette et al. Cloning and expression of the gene ecoding the Thermoanaerobacter ethanolicus 39E secondar-alcohol dehydrogenase and biochemical characterization of the enzyme. Biochem J., vol. 316, pp. 115-122, 1996.*

* cited by examiner

*Primary Examiner*—Celine Qian
*Assistant Examiner*—Jennifer Dunston
(74) *Attorney, Agent, or Firm*—Winston & Strawn LLP

(57) ABSTRACT

The present invention discloses the isolation and use of a specific bacterial promoter region suitable for use in constructs for the high level production of heterologous proteins. This promoter is derived from the bacterial gene encoding for alcohol dehydrogenase, in particular the alcohol dehydrogenase genes isolated from the thermophilic bacterial strain *T. brockii* and the mesophilic bacterial strain *Clostridium beijerinckii*. It is now disclosed that using either the intact promoter region or certain specific fragments consisting of at least a 88 bp DNA sequence in the upstream untranslated region of the bacterial alcohol dehydrogenase gene, operatively linked to the nucleic acid sequences encoding a heterologous protein, and insertion into a DNA plasmid or any other suitable vector system, heterologous genes can be expressed in high levels in host cells. Heterologous proteins or peptides can be expressed constitutively at high levels. The proteins are obtained in their active folded form.

9 Claims, 4 Drawing Sheets

Heterologous cDNAs expressed:

FGF2      468 bp
FGF9-2    437 bp
hColX-NC1 486 bp
FGF9-1    565 bp
FGFR3-Ex  662 bp

```
                            SEQUENCE LISTING

<160> NUMBER OF SEQ ID NOS: 24

<210> SEQ ID NO 1
<211> LENGTH: 200
<212> TYPE: DNA
<213> ORGANISM: Thermoanaerobacter brockii

<400> SEQUENCE: 1
aaatgctatt ttatcacaag agatttctct agttctttt tacttaaaaa aaccctacga    60
aattttaaac tatgtccgaa taaattattg ataaatttt aactatgtgc tattatatta   120
ttgcaaaaaa tttaacaatc atcgcgtaag ctagttttca cattaatgac ttatttagta   180
ttttaggagg tgttttaatg                                               200

<210> SEQ ID NO 2
<211> LENGTH: 88
<212> TYPE: DNA
<213> ORGANISM: Thermoanaerobacter brockii

<400> SEQUENCE: 2
ttatattatt gcaaaaaatt taacaatcat cgcgtaagct agttttcaca ttaatgactt    60
acccagtatt taggaggtg ttttacat                                        88

<210> SEQ ID NO 3
<211> LENGTH: 53
<212> TYPE: DNA
<213> ORGANISM: Thermoanaerobacter brockii

<400> SEQUENCE: 3
gttttcacat taatgactta cccagtattt taggaggtgt tttaatgatg aaa           53

<210> SEQ ID NO 4
<211> LENGTH: 200
<212> TYPE: DNA
<213> ORGANISM: Clostridium beijerinckii

<400> SEQUENCE: 4
aggcttatat tatatctcaa gcgaaatagc gatgaacagg cagatagtta taatataact    60
tcataatatg tttaaaatat tatttttgg catagtattt gcttaaatat atcatataag   120
actaaaacaa atttaaaaa taatttttta acgatgtttt tagactatta aaggaatatt   180
tttaaggagg aacatatttt                                               200

<210> SEQ ID NO 5
<211> LENGTH: 468
<212> TYPE: DNA
<213> ORGANISM: Homo sapien
```

```
<300> PUBLICATION INFORMATION:
<308> DATABASE ACCESSION NUMBER: NCBI/NM_002006
<309> DATABASE ENTRY DATE: 2003-01-15
<313> RELEVANT RESIDUES: (16)..(468)
<300> PUBLICATION INFORMATION:
<302> TITLE: Chimeric fibroblast growth factors
<310> PATENT DOCUMENT NUMBER: US5302702
<311> PATENT FILING DATE: 1993-02-26
<312> PUBLICATION DATE: 1994-04-12
<313> RELEVANT RESIDUES: (1)..(15)

<400> SEQUENCE: 5
atggcagaag gggaaatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaggagt gtgtgctaac      240 cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468

<210> SEQ ID NO 6
<211> LENGTH: 196
<212> TYPE: PRT
<213> ORGANISM: Homo sapien
<300> PUBLICATION INFORMATION:
<302> TITLE: Chimeric Fibroblast Growth Factors
<310> PATENT DOCUMENT NUMBER: US 5302702
<311> PATENT FILING DATE: 1993-02-26
<312> PUBLICATION DATE: 1994-04-12
<313> RELEVANT RESIDUES: (1)..(5)

<400> SEQUENCE: 6

Met Gly Gly Arg Gly Arg Gly Arg Ala Pro Glu Arg Val Gly Gly Arg
1               5                   10                  15

Gly Arg Gly Arg Gly Thr Ala Ala Pro Arg Ala Ala Pro Ala Ala Arg
                20                  25                  30

Gly Ser Arg Pro Gly Pro Ala Gly Thr Met Ala Ala Gly Ser Ile Thr
            35                  40                  45

Thr Leu Pro Ala Leu Pro Glu Asp Gly Gly Ser Gly Ala Phe Pro Pro
    50                  55                  60

Gly His Phe Lys Asp Pro Lys Arg Leu Tyr Cys Lys Asn Gly Gly Phe
65                  70                  75                  80

Phe Leu Arg Ile His Pro Asp Gly Arg Val Asp Gly Val Arg Glu Lys
                85                  90                  95

Ser Asp Pro His Ile Lys Leu Gln Leu Gln Ala Glu Glu Arg Gly Val
            100                 105                 110

Val Ser Ile Lys Gly Val Cys Ala Asn Arg Tyr Leu Ala Met Lys Glu
        115                 120                 125

Asp Gly Arg Leu Leu Ala Ser Lys Cys Val Thr Asp Glu Cys Phe Phe
    130                 135                 140

Phe Glu Arg Leu Glu Ser Asn Asn Tyr Asn Thr Tyr Arg Ser Arg Lys
145                 150                 155                 160

Tyr Thr Ser Trp Tyr Val Ala Leu Lys Arg Thr Gly Gln Tyr Lys Leu
                165                 170                 175

Gly Ser Lys Thr Gly Pro Gly Gln Lys Ala Ile Leu Phe Leu Pro Met
            180                 185                 190
```

-continued

Ser Ala Lys Ser
        195

<210> SEQ ID NO 7
<211> LENGTH: 30
<212> TYPE: DNA
<213> ORGANISM: Artificial Sequence
<220> FEATURE:
<223> OTHER INFORMATION: primer sequence for generating SEQ ID NO: 5

<400> SEQUENCE: 7
gcataggctc atatggcaga agggggaaatc                                    30

<210> SEQ ID NO 8
<211> LENGTH: 28
<212> TYPE: DNA
<213> ORGANISM: Artificial Sequence
<220> FEATURE:
<223> OTHER INFORMATION: primer sequence for generating SEQ ID NO: 5

<400> SEQUENCE: 8
ggatctggat ccttatcagc tcttagca                                       28

<210> SEQ ID NO 9
<211> LENGTH: 486
<212> TYPE: DNA
<213> ORGANISM: Homo sapien
<300> PUBLICATION INFORMATION:
<308> DATABASE ACCESSION NUMBER: NCBI/NM_000493.2[20a]
<309> DATABASE ENTRY DATE: 2002-01-19
<313> RELEVANT RESIDUES: (1)..(486)

<400> SEQUENCE: 9
gtcatgcctg agggttttat aaaggcaggc caaaggccca gtctttctgg gaccccctctt    60 gttagtgcca accaggggt aacaggaatg cctgtgtctg cttttactgt tattctctcc    120
aaagcttacc cagcaatagg aactcccata ccatttgata aaattttgta taacaggcaa   180
cagcattatg acccaaggac tggaatcttt acttgtcaga taccaggaat atactatttt   240
tcataccacg tgcatgtgaa agggactcat gtttgggtag gcctgtataa gaatggcacc   300
cctgtaatgt acacctatga tgaatacacc aaaggctacc tggatcaggc ttcagggagt   360
gccatcatcg atctcacaga aaatgaccag gtgtggctcc agcttcccaa tgccgagtca   420
aatggcctat actcctctga gtatgtccac tcctcttttct caggattcct agtggctcca   480
atgtga                                                              486

<210> SEQ ID NO 10
<211> LENGTH: 161
<212> TYPE: PRT
<213> ORGANISM: Homo sapien
<300> PUBLICATION INFORMATION:
<308> DATABASE ACCESSION NUMBER: NCBI/NP_000484.2
<309> DATABASE ENTRY DATE: 2002-01-19
<313> RELEVANT RESIDUES: (520)..(680)

<400> SEQUENCE: 10

Val Met Pro Glu Gly Phe Ile Lys Ala Gly Gln Arg Pro Ser Leu Ser
1               5                   10                  15

Gly Thr Pro Leu Val Ser Ala Asn Gln Gly Val Thr Gly Met Pro Val
            20                  25                  30

Ser Ala Phe Thr Val Ile Leu Ser Lys Ala Tyr Pro Ala Ile Gly Thr
        35                  40                  45

Pro Ile Pro Phe Asp Lys Ile Leu Tyr Asn Arg Gln Gln His Tyr Asp

```
            50                  55                  60
Pro Arg Thr Gly Ile Phe Thr Cys Gln Ile Pro Gly Ile Tyr Tyr Phe
 65                  70                  75                  80

Ser Tyr His Val His Val Lys Gly Thr His Val Trp Val Gly Leu Tyr
                 85                  90                  95

Lys Asn Gly Thr Pro Val Met Tyr Thr Tyr Asp Glu Tyr Thr Lys Gly
                100                 105                 110

Tyr Leu Asp Gln Ala Ser Gly Ser Ala Ile Ile Asp Leu Thr Glu Asn
            115                 120                 125

Asp Gln Val Trp Leu Gln Leu Pro Asn Ala Glu Ser Asn Gly Leu Tyr
        130                 135                 140

Ser Ser Glu Tyr Val His Ser Ser Phe Ser Gly Phe Leu Val Ala Pro
145                 150                 155                 160

Met

<210> SEQ ID NO 11
<211> LENGTH: 50
<212> TYPE: DNA
<213> ORGANISM: Artificial Sequence
<220> FEATURE:
<223> OTHER INFORMATION: primer sequence for generating SEQ ID NO: 9

<400> SEQUENCE: 11
acttacgtca tatgcaccat caccatcacc atgtcatgcc tgatggcttc           50

<210> SEQ ID NO 12
<211> LENGTH: 28
<212> TYPE: DNA
<213> ORGANISM: Artificial Sequence
<220> FEATURE:
<223> OTHER INFORMATION: primer sequence for generating SEQ ID NO: 9

<400> SEQUENCE: 12
acgtggatcc tcacatggga gccactag                                  28

<210> SEQ ID NO 13
<211> LENGTH: 384
<212> TYPE: DNA
<213> ORGANISM: Homo sapien
<220> FEATURE:
<221> NAME/KEY: misc_feature
<222> LOCATION: (1)..(3)
<223> OTHER INFORMATION: Arg codon changed to Met start codon
<300> PUBLICATION INFORMATION:
<308> DATABASE ACCESSION NUMBER: NCBI/NM_002010.1
<309> DATABASE ENTRY DATE: 2001-08-10

<400> SEQUENCE: 13
atgcagctat actgcaggac tggatttcac ttagaaatct cccccaatgg tactatccag    60
ggaaccagga agaccacag ccgatttggc attctggaat ttatcagtat agcagtgggc    120
ctggtcagca ttcgaggcgt ggacagtgga ctctacctcg ggatgaatga aaggggggag    180
ctgtatggat cagaaaaact aacccaagag tgtgtattca gagaacagtt cgaagaaaac    240
tggtataata cgtactcgtc aaacctatat aagcacgtgg acactggaag gcgatactat    300
gttgcattaa ataaagatgg accccgagag aagggactag gactaaacgc gcaccagaaa    360
ttcacacatt ttttacctag atga                                          384

<210> SEQ ID NO 14
<211> LENGTH: 145
<212> TYPE: PRT
```

```
<213> ORGANISM: Homo sapien
<220> FEATURE:
<221> NAME/KEY: MISC_FEATURE
<222> LOCATION: (1)..(1)
<223> OTHER INFORMATION: Arg replaced with Met
<220> FEATURE:
<221> NAME/KEY: MISC_FEATURE
<222> LOCATION: (1)..(1)
<223> OTHER INFORMATION: Arg replaced with Met start amino acid
<300> PUBLICATION INFORMATION:
<308> DATABASE ACCESSION NUMBER: NCBI/NP_002001
<309> DATABASE ENTRY DATE: 2001-08-10

<400> SEQUENCE: 14

Met Gln Leu Tyr Cys Arg Thr Gly Phe His Leu Glu Ile Phe Pro Asn
 1               5                  10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
    50                  55                  60

Glu Lys Leu Thr Gln Glu Cys Val Phe Arg Glu Gln Phe Glu Glu Asn
65                  70                  75                  80

Trp Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu Pro Arg Pro
        115                 120                 125

Val Asp Pro Asp Lys Val Pro Glu Leu Tyr Lys Asp Ile Leu Ser Gln
    130                 135                 140

Ser
145

<210> SEQ ID NO 15
<211> LENGTH: 33
<212> TYPE: DNA
<213> ORGANISM: Artificial Sequence
<220> FEATURE:
<223> OTHER INFORMATION: primer sequence for generating SEQ ID NO: 13

<400> SEQUENCE: 15
gggaattcca tatgcagcta tactgcagga ctg                                  33

<210> SEQ ID NO 16
<211> LENGTH: 30
<212> TYPE: DNA
<213> ORGANISM: Artificial Sequence
<220> FEATURE:
<223> OTHER INFORMATION: primer sequence for generating SEQ ID NO: 13

<400> SEQUENCE: 16
ggccctaggt catctaggta aaaaatgtgt                                      30

<210> SEQ ID NO 17
<211> LENGTH: 495
<212> TYPE: DNA
<213> ORGANISM: Homo sapien
<220> FEATURE:
<221> NAME/KEY: misc_feature
<222> LOCATION: (1)..(1)
<223> OTHER INFORMATION: first three bases changed to ATG strart codon
<300> PUBLICATION INFORMATION:
```

<308> DATABASE ACCESSION NUMBER: NCBI/NM_002010.1
<309> DATABASE ENTRY DATE: 2001-08-10

<400> SEQUENCE: 17

```
atgcccaggg gacccgcagt cacggacttg gatcatttaa aggggattct caggcggagg      60
cagctatact gcaggactgg atttcactta gaaatcttcc ccaatggtac tatccaggga     120
accaggaaag accacagccg atttggcatt ctggaattta tcagtatagc agtgggcctg     180
gtcagcattc gaggcgtgga cagtggactc tacctcggga tgaatgagaa ggggagctg     240
tatggatcag aaaaactaac ccaagagtgt gtattcagag aacagttcga agaaaactgg     300
tataatacgt actcgtcaaa cctatataag cacgtggaca ctggaaggcg atactatgtt     360
gcattaaata agatgggac cccgagagaa gggactagga ctaaacggca ccagaaattc     420
acacatttt tacctagacc agtggacccc gacaaagtac ctgaactgta taaggatatt     480
ctaagccaaa gttga                                                      495
```

<210> SEQ ID NO 18
<211> LENGTH: 164
<212> TYPE: PRT
<213> ORGANISM: Homo sapien
<220> FEATURE:
<221> NAME/KEY: MISC_FEATURE
<222> LOCATION: (1)..(1)
<223> OTHER INFORMATION: Leu of FGF9 changed to Met

<400> SEQUENCE: 18

```
Met Pro Arg Gly Pro Ala Val Thr Asp Leu Asp His Leu Lys Gly Ile
1               5                   10                  15

Leu Arg Arg Arg Gln Leu Tyr Cys Arg Thr Gly Phe His Leu Glu Ile
            20                  25                  30

Phe Pro Asn Gly Thr Ile Gln Gly Thr Arg Lys Asp His Ser Arg Phe
        35                  40                  45

Gly Ile Leu Glu Phe Ile Ser Ile Ala Val Gly Leu Val Ser Ile Arg
    50                  55                  60

Gly Val Asp Ser Gly Leu Tyr Leu Gly Met Asn Glu Lys Gly Glu Leu
65                  70                  75                  80

Tyr Gly Ser Glu Lys Leu Thr Gln Glu Cys Val Phe Arg Glu Gln Phe
                85                  90                  95

Glu Glu Asn Trp Tyr Asn Thr Tyr Ser Ser Asn Leu Tyr Lys His Val
            100                 105                 110

Asp Thr Gly Arg Arg Tyr Tyr Val Ala Leu Asn Lys Asp Gly Thr Pro
        115                 120                 125

Arg Glu Gly Thr Arg Thr Lys Arg His Gln Lys Phe Thr His Phe Leu
    130                 135                 140

Pro Arg Pro Val Asp Pro Asp Lys Val Pro Glu Leu Tyr Lys Asp Ile
145                 150                 155                 160

Leu Ser Gln Ser
```

<210> SEQ ID NO 19
<211> LENGTH: 33
<212> TYPE: DNA
<213> ORGANISM: Artificial Sequence
<220> FEATURE:
<223> OTHER INFORMATION: primer sequence for generating SEQ ID NO: 17

<400> SEQUENCE: 19

```
gggaattcca tatgcccagg ggacccgcag tca                                    33
```

<210> SEQ ID NO 20
<211> LENGTH: 30
<212> TYPE: DNA
<213> ORGANISM: Artificial Sequence
<220> FEATURE:
<223> OTHER INFORMATION: primer sequence for generating SEQ ID NO: 17

<400> SEQUENCE: 20
agctggatcc tcaactttgg cttagaatat                                   30

<210> SEQ ID NO 21
<211> LENGTH: 666
<212> TYPE: DNA
<213> ORGANISM: Homo sapien
<300> PUBLICATION INFORMATION:
<308> DATABASE ACCESSION NUMBER: NCBI/NM_000142
<309> DATABASE ENTRY DATE: 2001-02-21

<400> SEQUENCE: 21
atggagcgga tggacaagaa gctgctggcc gtgccggccg ccaacaccgt ccgcttccgc      60
tgcccagccg ctggcaaccc cactccctcc atctcctggc tgaagaacgg cagggagttc     120
cgcggcgagc accgcattgg aggcatcaag ctgcggcatc agcagtggag cctggtcatg     180
gaaagcgtgg tgcccctcgga ccgcggcaac tacacctgcg tcgtggagaa caagtttggc     240
agcatccggc agacgtacac gctggacgtg ctggagcgct cccgcaccg gcccatcctg       300 caggcggggc tgccggccaa ccagacggcg gtgctgggca cgacgtgga gttccactgc      360 aaggtgtaca gtgacgcaca gccccacatc cagtggctca gcacgtgga ggtgaacggc      420 agcaaggtgg gcccggacgg cacaccctac gttaccgtgc tcaagacggc gggcgctaac     480
accaccgaca aggagctaga ggttctctcc ttgcacaacg tcacctttga ggacgccggg     540 gagtacaccct gcctggcggg caattctatt gggtttttctc atcactctgc gtggctggtg    600
gtgctgccag ccgaggagga gctggtggag gctgacgagg cgggctgtgt gtatgcaggc     660
atctga                                                              666

<210> SEQ ID NO 22
<211> LENGTH: 377
<212> TYPE: PRT
<213> ORGANISM: Homo sapien
<220> FEATURE:
<221> NAME/KEY: MISC_FEATURE
<222> LOCATION: (371)..(371)
<223> OTHER INFORMATION: Ser 371 replaced with Cys, to mimic
      Thantophoric Dysplasia phenotype
<300> PUBLICATION INFORMATION:
<308> DATABASE ACCESSION NUMBER: NCBI/NP_000133.1
<309> DATABASE ENTRY DATE: 2001-02-21
<313> RELEVANT RESIDUES: (1)..(377)

<400> SEQUENCE: 22

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

-continued

```
Gly Gly Gly Pro Met Gly Pro Thr Val Trp Val Lys Asp Gly Thr Gly
 65                  70                  75                  80

Leu Val Pro Ser Glu Arg Val Leu Val Gly Pro Gln Arg Leu Gln Val
                 85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Cys Val Tyr Ala Gly Ile Leu
    370                 375
```

<210> SEQ ID NO 23
<211> LENGTH: 35
<212> TYPE: DNA
<213> ORGANISM: Artificial Sequence
<220> FEATURE:
<223> OTHER INFORMATION: primer sequence for generating SEQ ID NO: 21

<400> SEQUENCE: 23
gctagtgaca tatggagcgg atggacaaga agctg    35

<210> SEQ ID NO 24
<211> LENGTH: 40
<212> TYPE: DNA

```
<213> ORGANISM: Artificial Sequence
<220> FEATURE:
<223> OTHER INFORMATION: primer sequence for generating SEQ ID NO: 21

<400> SEQUENCE: 24
agctggatcc ttatgcatac acacagcccg cctcgtcagc                              40
```

THERMOANAEROBACTER BROCKII ALCOHOL DEHYDROGENASE PROMOTER FOR EXPRESSION OF HETEROLOGOUS PROTEINS

CROSS-REFERENCE TO RELATED APPLICATIONS

This application is a continuation of the U.S. National Stage designation of International application PCT/IL01/00870, filed on Sep. 16, 2001, the content of which is expressly incorporated herein by reference thereto.

FIELD OF THE INVENTION

The field of the invention relates to a promoter element sequence derived from a bacterial gene that promotes high level of expression of proteins and polypeptides in cell cultures enabling high-yield expression of heterologous proteins in vitro, obtained in the active conformation, as exemplified for genes encoding FGF.

BACKGROUND OF THE INVENTION

Prokaryotic culture systems such as *Escherichia coli* (*E. coli*) or other bacterial strains, which are considered fast expression systems, are most often the first choice for overproduction of proteins (Current Opinion in Biotechnology 10, 411, 1999). These systems have several known limitations, including problems in expression of large proteins, low solubility of over-expressed proteins and non-full-length gene products due to different codon usage between eukaryotes and prokaryotes, as well as lack of glycosylation. Despite these limitations, the progress made in resolving transcription, translation and protein folding processes as well as availability of improved genetic tools, make bacteria highly suitable for the expression of complex eukaryotic proteins.

Certain methods for increasing the yield of expressed proteins by variations in the culture conditions have been disclosed in yeast (EP 213 029) and in bacteria (WO 91/13156). EP 213 029 discloses the increased yield of a galactose-regulated gene product by replenishing the culture medium with fresh medium before adding the galactose to induce expression of the foreign protein. WO 91/13156 discloses the enhanced recovery of specific proteins by culturing bacterial cultures at least to the late stationary phase, without specific genetic manipulation of the regulatory genes encoded along with the recombinant protein. This disclosure neither teaches nor suggests any general mechanism for the overproduction and seems to be specific to a very restricted group of genes.

Regulation of gene expression has been found to be exerted mainly through regions of untranslated upstream DNA sequences. Deletions of material upstream or downstream from a suspected control region can be used to identify the boundaries of the promoter. Promoter regions including enhancers are characterized by their ability to bind to RNA polymerase and other activating proteins, and generally contain recognition sites for the various proteins.

One of the most essential elements is the promoter used to express the heterologous genes. U.S. Pat. No. 6,068,991 discloses a novel expression vector containing the tac promoter, based on the endogenous *E. coli* GroESL operon, used for over expression of heterologous genes in *E. coli*. Some of the other more frequently used strong promoters for the expression of heterologous genes are the promoters from $P_L$, tac, trp, trc and the T7 promoter. The promoters used are generally regulatable. This feature is essential if the target protein to be expressed is toxic to the host. In general, the stronger the promoter, the more RNA will be transcribed from the DNA leading to the accumulation of messenger RNA. Besides strong regulatable promoters, other elements are also involved in the expression of heterologous genes. The efficiency of the translation is involved in maximizing the expression of heterologous genes. The efficiency of translation can be affected by the mRNA 5'-terminus sequences as well as by the 5' end hairpin structure of the mRNA. Generally, a functional ribosome binding site containing a Shine-Delgarno (SD) sequence properly positioned to an AUG initiation codon is essential for efficient translation. Variation in the distance between the SD sequence and the AUG codon are known to affect mRNA translation. Studies have also shown when the SD sequence or the AUG initiation codon is sequestered in a double-stranded region of the mRNA, translation is less efficient due to the blocking of the accessibility of these sequences to the ribosome. Some other factors that have been reported to affect the efficient expression of heterologous genes are the stability of the messenger RNAs, the susceptibilities of the protein products to proteolysis and the effect of the host genetic background. Although there is a wealth of information about the elements that affect the overall efficiency of a plasmid based expression system, there are other elements that have not been studied which may be involved in the expression of heterologous genes.

Another problem presented by protein expression in prokaryotes is the three dimensional folding of proteins in an active form. Under some conditions, certain heterologous proteins expressed in large quantities from bacterial hosts precipitate within the cells in dense aggregates or inclusion bodies, and constitute a significant portion of the total cell protein. Recovery of the protein from these bodies has presented numerous problems, such as how to separate the protein encased within the cell from the cellular material and proteins harboring it, and how to recover the inclusion body protein in biologically active form. The recovered proteins are often predominantly biologically inactive because they are folded into a three-dimensional conformation different from that of the active protein. Methods for refolding the proteins into the correct, biologically active conformation are tedious, costly and time consuming, as is well known in the art.

The present invention is an unexpected result stemming from research related to structural elements that confer thermostability to bacteria. The two genes encoding for the enzyme alcohol dehydrogenase from the thermophilic bacterium *Thermoanaerobacter brockii* and from the mesophile *Clostridium beijerinckii* (TBADH and CBADH, respectively) were isolated and compared. The genes coding for the enzymes alcohol dehydrogenase from thermophilic and mesophilic bacteria (TBADH and CBADH) have been successfully cloned, sequenced and expressed in *E. coli* strain TG1 using the plasmids pBS-M105/2 and pBS-P89. The level of the expressed enzymes inserted in pBluescript II KS(+) was 30-50 fold higher than in the native bacterium *T. brockii* or *C. beijerinckii* (Anaerobe 3, 259, 1997).

It was neither taught nor suggested in the background references that the overexpression attained for the thermophilic alcohol dehydrogenase could be obtained for other proteins cloned into an expression system, utilizing the bacterial ADH promoter. Furthermore, it is neither suggested nor taught that an expression system using said prokaryotic ADH promoter could yield eukaryotic heterologous proteins in their active folded form.

Fibroblast Growth Factors

Fibroblast Growth Factors (FGF's) encompass a family of at least 23 factors, which have an amino acid sequence identity ranging between 17-72%. FGF's are potent mitogens for a wide variety of cell types in tissue culture as well as in-vivo, and are regulators of differentiation of endothelial cells and neuronal cells. FGF's are expressed in a strict temporal and spatial pattern during development and have important roles in patterning and limb formation. The biological effects of FGF are initiated by binding to FGF receptors (FGFRs), phosphorylation of a trans-membrane tyrosine kinase and triggering the intracellular cascade of signal transduction.

Because of their role in growth regulation, the isolation, cloning and expression of FGF receptor ligands are extremely important for developing medicaments for the treatment of various disorders and in particular those of bone and cartilage.

Current art teaches that attempts to express synthetic DNA fragments encoding the entire reading frame of human fibroblast growth factor-1 (HBGF-1beta), and its amino terminal truncated form (HBGF-1 alpha) in *Escherichia coli* under the control of the trp-lac resulted in high yield and biologically active HBGF-1 alpha. (Biochem. Biophys. Acta 1090, 293, 1991) The HBGF-1 beta was highly expressed using T7 polymerase expression vector.

A synthetic gene encoding human basic FGF has been cloned and expressed in *E. coli* as a biologically active protein using the expression vector pLCII downstream from the strong PL promoter (J. Biotechnol. 22, 299, 1992).

There is an unmet need for and it would be advantageous to have a high yield expression system that can be used to express various FGF agonists, FGF antagonists, FGF mutants or FGF chimeras having therapeutic value for treating various diseases.

SUMMARY OF THE INVENTION

It is an object of the present invention to provide a high yield expression system suitable for use in constructs for transfection of cloned heterologous genes into host cells.

The present invention discloses the identification, construction and use of a specific promoter element derived from a bacterial gene encoding alcohol dehydrogenase enabling high expression of cloned heterologous genes ligated thereto.

The present invention further discloses the surprising finding that the expression of the heterologous genes operatively linked to said promoter and cloned into an expression vector used for transfection of host cells, may be constitutively expressed. According to alternative embodiments an inducible element may be included in the expression system.

In currently more preferred embodiments according to the present invention use of a specific promoter constructed from the genes encoding for alcohol dehydrogenase of the preferred bacterial strains *Thermoanaerobacter brockii*, and *Clostridium beijerinckii* is disclosed.

The present invention is based on the surprising finding that the upstream flanking region of the genes encoding for *Thermoanaerobacter brockii* alcohol dehydrogenase (TBADH), and *Clostridium beijerinckii* alcohol dehydrogenase (CBADH), and fragments of said flanking region can provide high yields of heterologous protein expression when cloned into certain DNA plasmids.

By way of exemplification the ligation of said promoter to structural genes for Fibroblast Growth Factors and their receptors or fragments thereof, and for certain collagen subtypes is disclosed thus enabling its high expression in *E.Coli* strains as exemplified by but not limited to TG1, TG2, DH5-alpha strains. It must be stressed however, that the principles of the invention are applicable to all prokaryotic cell cultures including commercially available bacterial strains as well as genetically engineered bacterial strains.

The present invention discloses the nucleic acid sequence comprising the complete promoter region of TBADH as denoted in SEQ ID NO: 1.

```
(encoding the promoter region of TBADH consisting of 200 bp)
AAATGCTATT TTATCACAAG AGATTTCTCT AGTTCTTTTT TACTTAAAAA AACCCTACGA   SEQ ID NO:1

AATTTTAAAC TATGTCCGAA TAAATTATTG ATAAATTTTT

AACTATGTGC TATTATATTA TTGCAAAAAA TTTAACAATC ATCGCGTAAG CTAGTTTTCA

CATTAATGAC TTATTTAGTA TTTTAGGAGG TCTTTTAATG
```

The present invention further discloses the nucleic acid sequence comprising the fragment of promoter region of TBADH as denoted in SEQ ID NO: 2.

```
(encoding an 88 bp fragment of TBADH)
                                                   SEQ ID NO:2
TTATATTATT GCAAAAAATT TAACAATCAT CGCGTAAGCT

AGTTTTCACA TTAATGACTT ACCCAGTATT TTAGGAGGTG

TTTTACAT
```

The present invention further discloses the nucleic acid sequence comprising the deleted fragment of promoter region of TBADH as denoted in SEQ ID NO:3.

```
(encoding a 53 bp fragment of TBADH)
                                                   SEQ ID NO:3
GTTTTCACAT TAATGACTTA CCCAGTATTT TAGGAGGTGT

TTTAATGATG AAA
```

The present invention further discloses the nucleic acid sequence comprising the complete promoter region of CBADH as denoted in SEQ ID NO:4 (encoding the entire promoter of CBADH consisting of 200 bp).

```
AGGCTTATAT TATATCTCAA GCGAAATAGC GATGAACAGG

CAGATAGTTA TAATATAACT TCATAATATG TTTAAAATAT

TATATTTTGG CATAGTATTT
```

-continued

```
GCTTAAATAT ATCATATAAG ACTAAAACAA ATTTTAAAAA

TAATTTTTTA ACGATGTTTT TAGACTATTA AAGGAATATT

TTTAAGGAGG AACATATTTT
```

It is an object of the present invention to provide vectors containing these promoter sequences that can produce high yield of heterologous proteins in host cells transfected with such vectors.

It is further an object of the present invention to provide methods of obtaining high level production of a heterologous protein by ligating the DNA encoding said protein under control of the ADH promoter into such high copy DNA plasmids and transfecting them into host cells.

It is yet another object of the present invention to provide a method for obtaining expression of heterologous proteins in their active folded form. In particular it is the object of the present invention to provide methods for obtaining high level expression of heterologous proteins in their active folded form.

Within the scope of the present disclosure, culture conditions are provided for supporting the growth of host cells under which the expression of heterologous proteins can be optimally regulated.

BRIEF DESCRIPTION OF THE FIGURES

The present invention will be best understood in relation to the following figures wherein.

DETAILED DESCRIPTION OF THE INVENTION

Figure 1:
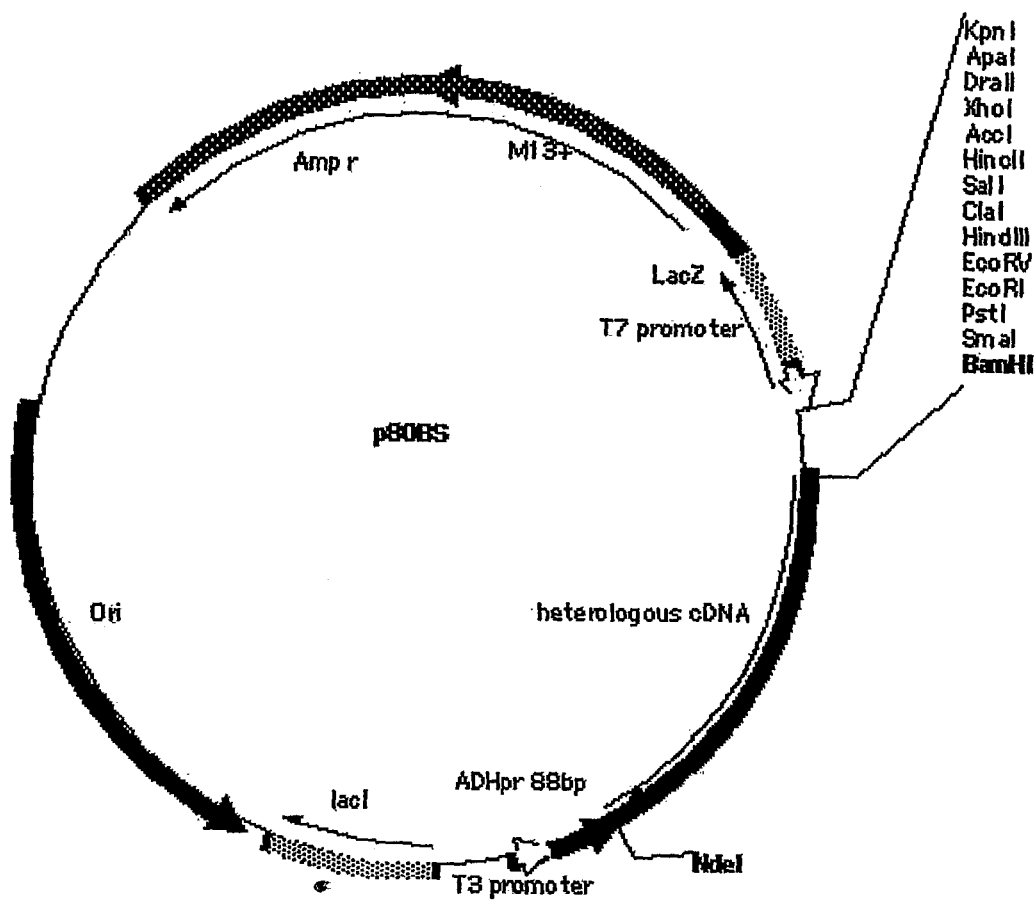
FIG. 1 shows the DNA construct of a 88 bp fragment of the TBADH promoter operatively linked to a heterologous DNA sequence encoding for:
  an FGF2 consisting of 468 bp (P89BS-FGF2);
  a fragment of FGF9 consisting of 384 bp (P89BS-FGF-9-2);
  a human collagen X NCI domain consisting of 486 bp (P89BS-hColX-NCI);
  a fragment of FGF9 consisting of 495 bp (P89BS-FGF-9-1);
  the extracellular IgG II and III domains of human FGFR3 consisting of 663 bp (P89BS-FGFR3-Ex).

It is an object of the present invention to provide methods for the enhanced production of heterologous proteins in cultures of cells. The present invention provides means for the enhanced production of such heterologous proteins by introducing a novel promoter element into DNA sequences encoding the protein of choice.

The present invention further provides a method for the constitutive high-level expression of the heterologous proteins, without the need to use expensive inducers such as isopropyl-beta-D-thiogalactopyranoside (IPTG). Advantages in using a constitutive expression vector include elimination of the need to add an inducer to induce the system to express the heterologous gene products. This can decrease the cost of goods and simplify the process of protein expression so that adjusting for optimal concentrations of IPTG and the optimal time to add the inducer to yield optimal expression of the gene product is eliminated. The cloning of heterologous genes in constitutive expression vectors will yield more heterologous gene products as the gene products are accumulated from the very beginning of the cell growth. In cases where the expression is constitutive, lac repressor molecules such as IPTG or lactose may minimally induce the heterologous proteins.

As used herein and in the claims the term heterologous protein refers to any foreign protein expressed as a result of introducing its encoding gene into a plasmid suitable for transfection into host cells.

Specific examples of proteins that can be expressed in this system include but are not limited to growth factors and polypeptide hormones and other proteins that can stimulate various cellular processes concerning cell division, cell growth, cell proliferation, differentiation, coagulation, and the like. The following non-limiting examples illustrate various types of growth factors and growth factor receptors, protein and peptide hormones and receptors, cytokines and cytokine receptors, agonists or antagonist of a growth factor or hormone receptor that can be used: proinsulin, insulin like growth factor-1 and insulin like growth factor-2, insulin A-chain; insulin B-chain, platelet derived growth factor, epidermal growth factor, fibroblast growth factor, nerve growth factor or other neurotrophic factors such as brain-derived neurotrophic factor (BDNF), neurotrophin-3, -4, -5, or -6 (NT-3, NT-4, NT-5, or NT-6), vascular endothelial growth factor, colony stimulating factor e.g., M-CSF, GM-CSF, and G-CSF, transforming growth factor and TGF-β related proteins such as inhibin, activin or Mullerian-inhibiting substance, tumor necrosis factor, bone morphogenic protein, angiotensin, calcitonin, glucagons, leptin, parathyroid hormone, growth hormone, growth hormone releasing factor, mouse gonadotropin-associated peptide, gonadotropin, relaxin A-chain, relaxin B-chain, prorelaxin, a natriuretic peptide such as atrial natriuretic factor and brain natriuretic peptide-32, a hematopoieitic cytokine such as erythropoietin, granulocyte-colony stimulating factor (G-CSF) or leukemia inhibitory factor (LIF), interleukins (ILs), e.g., IL-1 to IL-17 or an interferon such as interferon-alpha, -beta, and -gamma or their corresponding receptors, or other cytokines such as RANTES, MIP-1 alpha or MIP-1 beta.

Additional heterologous proteins can be a pituitary hormone such as bombesin, corticotropin releasing factor (CRF), follicle stimulating hormone, oxytocin, somatotropin or vasopressin; a clotting factor such as factor VIIIC, factor IX, tissue factor, and von-Willebrand factor; an anti-clotting factor such as Protein C; a plasminogen activator such as urokinase or tissue-type plasminogen activator, including human tissue-type plasminogen activator (t-PA) or thrombin; an enzyme such as caspases, calpains, cathepsins, DNase, enkephalinase, matrix metalloproteinases (MMP) superoxide dismutase and protein kinases or an enzyme inhibitor exemplified by plasminogen activated inhibitor-1 or cathepsin inhibitor; an extracellular matrix protein such as a collagen or a fibronectin; a serum albumin such as human serum albumin; a microbial protein, such as beta-lactamase; a CD protein such as CD-3, CD-4, CD-8, and CD-19; immunotoxins; a surface membrane proteins; a T-cell receptor; a viral antigen such as, for example, a portion of the AIDS envelope; transport proteins; regulatory proteins; antibodies; and fragments of any of the above-listed polypeptides. Currently most preferred examples of proteins expressed using the high yield expression system includes, but is not limited to: FGF9, FGF-9-2, FGF2, mouse Collagen type X NCI domain, human Collagen type X NCI domain, human collagen VIII, and FGF receptor 3 (FGFR3) extracellular domain.

As used herein, and in the claims the term protein folding refers to proteins or polypeptides that assume a secondary, tertiary, and/or quaternary structure while maintaining their biological activity equivalent to the native proteins or enhanced biological activity as measured by cell proliferation, cell growth inhibition, and activation of down stream signaling.

As used herein and in the claims the terms high level expression or elevated protein production are used interchangeably and refer to the expression of a heterologous protein under the regulation of the constructed expression vector which is measured relative to the level of protein production under the regulation of the native endogenous promoter, lacking the DNA elements conferring high expression capabilities.

As used herein and in the claims the term expression vector refer to any plasmid or phage or any other vectors known in the art, which serve the function of transfection of a host cell with an heterologous DNA sequence and its expression in said host cell. The expression vectors preferably have an origin of replication and a nucleic acid sequence coding for a selectable marker. The particular selectable marker used is not critical provided the marker allows for phenotypic selection in transformed host cells. Preferred selectable markers are antibiotic resistance. Examples of antibiotic resistance markers include ampicillin, tetracycline, chloramphenicol, kanamycin, gentamycin, nalidixic acid, rifampicin, spectinomycin, streptomycin, neomycin phosphotransferase, and the like.

The most preferred vectors that can be used are: pET9dPGA as well as the high copy DNA plasmids as exemplified but not limited to by pBluescript family (including but not limited to pBMS2000PGA, pBMS1000PGA, pBMS2000HGCA, pBMS200075GCA, pBMS2000.103GCA, pBMS2000GCA, pBMS1999GCA, pBMS1000GCA, and the like).

Expression vectors may be introduced into host cells by various methods known in the art. For example, transfection of host cells with expression vectors can be carried out by the calcium chloride or rubidium chloride precipitation method. However, other methods for introducing expression vectors into host cells, such as electroporation or the like, can also be employed.

Once an expression vector has been introduced into an appropriate host cell, the host cell may be cultured under conditions permitting expression of the desired protein or polypeptide. As used herein and in the claims the term host cell culture refers to a culture of cells that can be either commercially available or genetically engineered, which are grown in a medium that supports their growth. Alternatively, the heterologous protein can be expressed using the high level expression system in a cell free system.

Suitable host cells are prokaryotic cells which are preferably biologically pure. Suitable prokaryotic host cells include, for example, *Escherichia coli, Bacillus subtilus* and *Salmonella typhimurum* cells. The most preferred host cell of the invention are strains derived from the bacteria *E. coli* such as DH5-alpha, TG1, TG2. It is acknowledged that certain bacterial strains may be superior to others, as will be readily ascertained by the artisan without undue experimentation.

Host cells containing an expression vector of the invention may be identified by one or more of the following six general approaches: (a) DNA-DNA hybridization; (b) the presence or absence of marker gene functions; (c) assessing the level of transcription as measured by the production of mRNA transcripts in the host cells; (d) detection of the gene product immunologically; (e) complementation analysis; and (f) enzyme assay, enzyme assay being the preferred method of identification.

High expression levels of heterologous proteins may be achieved by changing the codon usage into a prokaryotic DNA codon, thus minimizing the problems arising from rare codon usage. Furthermore, certain additives such as IPTG, arabinose, glycerol and the like may achieve enhanced expression, by inducing a "gentle stress" thereby improving protein folding.

Growth of the host cells may be achieved by one of ordinary skill in the art by the use of an appropriate medium. Appropriate media for growing host cells include those which provide nutrients necessary for the growth of the cells. A typical medium for growth includes necessary carbon sources, nitrogen sources, and trace elements. Inducers may also be added. The term "inducer", as used herein, includes any compound enhancing formation of the desired protein or peptide. Carbon sources may include sugars such as glucose, sucrose, lactose, galactose, raffinose, and the like; nitrogen sources include yeast extract, casamino acids, N-Z amine, bactotryptone, and the like.

Regulation of temperature and velocity of culture shaking or stirring is adjusted to maintain viable cells in culture. The pH of the medium may be for example about 5-8 and is preferably adjusted to or maintained at about 6.8 to 7.6. These and other factors for the optimization of process parameters will be recognized by the skilled artisan in the field to which the invention pertains.

As used herein and in the claims the term promoter element refers to regulatory DNA sequences in the upstream untranslated region of the heterologous gene, which are operatively linked to the DNA sequence coding for all or part of the heterologous gene sequence desired to be expressed, and which are effective in promoting the high level of expression of the protein encoded by said heterologous gene. The term "operatively linked" means that the regulatory DNA sequences are capable of directing the replication and/or the expression of the DNA sequence coding for all or part of the protein desired to be expressed.

While the promoter enhancing the high expression level is an essential element of the invention, it is modular and can be used in different contexts. It will be appreciated by one skilled in the art, that the promoter disclosed in this invention is of prime importance, and can be used for high yield expression of any heterologous gene ligated to this promoter.

The genetic element more preferably used to increase the expression levels of a heterologous protein is the promoter from the bacterial alcohol dehydrogenase gene. According to the currently most preferred embodiments of the invention the promoter is cloned from the alcohol dehydrogenase genes of the bacteria *T. brockii* and *Clostridium beijerinckii*.

According to the present invention the constructed promoter is effective when used for example in combination with a heterologous gene encoding a mammalian protein including but not limited to the FGF family of molecules.

According to the present invention the genetic information for the production of the protein molecules of interest is introduced into the host cells by an appropriate vector as is known in the art. The present invention provides information that will enable the skilled artisan to prepare constructs of genetic material comprising a novel expression system that may be used to provide high yield of proteins encoded by such genetic material.

It was previously shown that alcohol dehydrogenase from the bacteria *T. brockii* is a constitutively expressed gene yielding limited amounts of expressed native protein. Specific expression promoting elements are now disclosed for the first time to contain certain nucleotide sequences residing in the flanking region outside the initiation codon conferring high yield of heterologous protein expression.

It is now disclosed that the promoter in the flanking regions of the bacterial gene encoding alcohol dehydrogenase can be used to produce high yield expression of heterologous genes cloned into expression vectors under the control of this promoter. It is further disclosed that certain deletions or fragments of the flanking upstream region of the gene encoding the cloned bacterial alcohol dehydrogenase are also capable of inducing over expression of heterologous proteins in certain host cells.

According to the present invention the genetic information for the high level production of protein molecules of interest is introduced into the host cells by means of an appropriate vector as is known in the art. The present invention provides information to the skilled artisan to prepare constructs of the genetic material comprising the high expression promoter region ligated to any heterologous gene encoding a protein of interest.

It is anticipated that the expression system herein disclosed will be appropriate for high level expression of any cloned gene whether prokaryotic or eukaryotic in origin, which may be usefully expressed in bacterial hosts.

The Expression System:

DNA sequences encoding the promoter element capable of inducing high expression levels of proteins, will most advantageously be placed upstream of the translational start site (ATG) of the gene to be expressed. In a preferred embodiment, such promoter element that is exemplified herein, denoted as SEQ ID NO: 1 through SEQ ID NO: 4, is selected for expressing the genes of interest in bacterial cells.

In a most preferred embodiment, this promoter element is placed immediately upstream of the translational start site (ATG) of the gene to be expressed.

In one currently most preferred embodiment according to the present invention the ADH promoter and the heterologous gene under its control are ligated into the Bluescript vector.

Signal Sequence

According to one embodiment of the present invention secretion of the protein out of the cell is preferred. In this embodiment the construct will comprise a signal sequence to effect secretion as is known in the art. In a more preferred embodiment a signal sequence recognized in the host cells can be incorporated together with the promoter element, as exemplified herein. As will be recognized by the skilled artisan, the appropriate signal sequence should be placed immediately downstream of the translational start site (ATG), and in frame with the coding sequence of the gene to be expressed.

Host Cells:

Introduction of the construct into the microorganism or cell line of choice is accomplished by any conventional method for transfection, infection or the like as is known in the art.

Stable transfectants and stable cell lines may be derived from the transfected cells in appropriate cases, in order to conveniently maintain the genotype of interest.

Cell growth is accomplished in accordance with the cell type, using any standard growth conditions as may be suitable to support the growth of the specific cell line.

In a more preferred embodiment, the organism of choice for expressing the heterologous protein of interest will be, but is not limited to *E. coli*, although, any other prokaryotic cells may be used as appropriate organism of choice.

Protein Production:

The product may be accumulated in the cell, in which case the specific concentration of the product is gradually increased due to the continuous synthesis of the product and concomitant decrease in the synthesis of other proteins. The high specific concentration of the product should be especially beneficial in the purification of said product. It will be appreciated by the skilled artisan that it is necessary to optimize the process parameters to obtain maximal product yield and/or optimal specific concentration of protein in the host cells.

In other embodiments wherein the product is secreted out of the cells, the cells may be harvested by non-disruptive means, as are known in the art, and the depleted medium containing the secreted product is recovered. These cells can then be resuspended in fresh medium that does not support cell growth or supports little growth. Cells continue to secrete the product into this second medium, and subsequent batches of fresh medium for as long as the cells sustain the product synthesis. It will be appreciated by one skilled in the art that the mechanisms of collecting the medium or the cells can be manipulated in terms of process parameters to yield the optimized efficiency for any particular organism, and for any particular product.

The method of using the invention will be modified in accordance with the system that is selected according to the current principles that are known in the art of recombinant protein production. The present disclosure also teaches various means to exploit the commercial potential of these high yield expression elements.

EXAMPLES

Cloning and Construction of p89BS Plasmid

The plasmid p89BS was constructed by a series of digestions of *T. brockii* genomic DNA with restriction endonucleases, as described briefly. The *T. brockii* ADH gene was located on an EcoRI digest (2700 bp), and the fragment was first cloned into the EcoRI site of pBluescript II. XbaI digestion of a positive clone produced a smaller (1673 bp) DNA fragment containing the entire TB ADH gene, which was ligated to XbaI-digested pBluescript II to form the plasmid pBS-M105/2. The insert was composed of the DNA encoding the 352 amino acid residues of TBADH and flanking regions of 249 nuceotides upstream of the initiation codon and 342 nucleotides downstream of (and including) the termination codon. PBS-P89 was a deletion mutant in which the upstream region was limited to 89 bases preceding the initiation codon for the TBADH gene, and the shortened fragment was cloned into the ScaI-XbaI sites of pBluescriptII SK(+). Using site directed mutagenesis, ATGATG (−3 up to +3 in FIG. 1) were mutated into CATATG, thus constructing the NdeI site at the 5' starting codon while a GGATCC BamHI site was constructed right after the TGA stop codon, thus forming single unique NdeI-BamHI sites, similar to pET vector systems.

Construction of Plasmid Carrying the Promoter Element

PCR-generated DNA fragments encompassing the coding region of a number of proteins were produced having the NdeI-BamHI sites at the 5' and 3' ends respectively. To adapt the N-terminus-encoding sequence to the vector, the forward primer (28 bases long) corresponded to the coding sequence for amino acid residues 1 through 8 of TBADH and had an NdeI site added to the 5' end. The reverse primer (29 bases long) corresponded to the stop codon and the next 20 bases of the complementary strand, and a BamH1 site was added to the 3' end.

Construction of P89BS-FGF-2

PCR reaction was as follows:

| | |
|---|---|
| 1. 94° C. | 3 min |
| 2. 94° C. | 30 sec |
| 3. 56° C. | 1 min |
| 4. 72° C. | 1 min |
| 5. 72° C. | 5 min | with 30 cycles going between steps 2-4. The PCR reaction was separated on a 2% agarose gel, resulting in a band of size 468 bp, which was later purified from the gel (Qiaquick gel extraction kit, Qiagen). The purified fragment was subjected to endonuclease digestion using Nde I and BamHI (MBI Fermentas) restriction enzymes (2 hr at 37° C.). The digested PCR reaction was purified from a 2% agarose gel

```
Human FGF-2 gene having 468 bp with the following sequence herein denoted:
                                                           SEQ ID NO:5
ATGGCAGAAG GGGAAATCAC CACGCTGCCC GCCTTGCCCG AGCATGGCGG CAGCGGCGCC

TTCCCGCCCG GCCACTTCAA GGACCCCAAG CGGCTGTACT GCAAAAACGG GGGCTTCTTC

CTGCGCATCC ACCCCGACGG CCGAGTTGAC GGGGTCCGGG AGAAGAGCGA CCCTCACATC

AAGCTACAAC TTCAAGCAGA AGAGAGAGGA GTTGTGTCTA TCAAAGGAGT GTGTGCTAAC

CGTTACCTGG CTATGAAGGA AGATGGAAGA TTACTGGCTT CTAAATGTGT TACGGATGAG

TGTTTCTTTT TTGAACGATT GGAATCTAAT AACTACAATA CTTACCGGTC AAGGAAATAC

ACCAGTTGGT ATGTGGCACT GAAACGAACT GGGCAGTATA AACTTGGATC CAAAACAGGA

CCTGGGCAGA AAGCTATACT TTTTCTTCCA ATGTCTGCTA AGAGCTGA

With the protein sequence going from Met1 to Ser155 denoted herein:
                                                           SEQ ID NO:6
   1  Met Ala Glu Gly Glu Ile Thr Thr Leu Pro Ala Leu Pro Glu Asp    15

16  Gly Gly Ser Gly Ala Phe Pro Pro Gly His Phe Lys Asp Pro Lys    30

31  Arg Leu Tyr Cys Lys Asn Gly Gly Phe Phe Leu Arg Ile His Pro    45

46  Asp Gly Arg Val Asp Gly Val Arg Glu Lys Ser Asp Pro His Ile    60

61  Lys Leu Gln Leu Gln Ala Glu Glu Arg Gly Val Val Ser Ile Lys    75

76  Gly Val Cys Ala Asn Arg Tyr Leu Ala Met Lys Glu Asp Gly Arg    90

91  Leu Leu Ala Ser Lys Cys Val Thr Asp Glu Cys Phe Phe Phe Glu   105

106  Arg Leu Glu Ser Asn Asn Tyr Asn Thr Tyr Arg Ser Arg Lys Tyr   120

121  Thr Ser Trp Tyr Val Ala Leu Lys Arg Thr Gly Gln Tyr Lys Leu   135

136  Gly Ser Lys Thr Gly Pro Gly Gln Lys Ala Ile Leu Phe Leu Pro   150

151  Met Ser Ala Lys Ser
```

FGF-2 gene having a NdeI site at the 5' and BamHI site at the 3' end was generated by Polymerase chain reaction (PCR) using the primers:

and cloned in p89BS pre-digested with Nde I and BamHI using T4 Ligase (MBI Fermentas) (16 hr 20° C.), forming the construct p89BS-bFGF.

```
(35341) FGF-2Nde    5'-GCATAGGCTCATATGGCAGAAGGGGAAATC-3' denoted herein. SEQ ID NO:7

(35342) fgf-2BamHI  5'-GGATCTGGATCCTTATCAGCTCTTAGCA-3'  denoted herein.  SEQ ID NO:8
```

Construction of p89BS-hColX-NCI

```
Human collagen type X NCI domain gene having 486 bp with the following
sequence herein denoted:
                                                         SEQ ID NO:9
         GTC ATGCCTGAGG GTTTTATAAA GGCAGGCCAA AGGCCCAGTC TTTCTGGGAC

CCCTCTTGTT AGTGCCAACC AGGGGGTAAC AGGAATGCCT GTGTCTGCTT TTACTGTTAT

TCTCTCCAAA GCTTACCCAG CAATAGGAAC TCCCATACCA TTTGATAAAA TTTTGTATAA

CAGGCAACAG CATTATGACC CAAGGACTGG AATCTTTACT TGTCAGATAC CAGGAATATA

CTATTTTTCA TACCACGTGC ATGTGAAAGG GACTCATGTT TGGGTAGGCC TGTATAAGAA

TGGCACCCCT GTAATGTACA CCTATGATGA ATACACCAAA GGCTACCTGG ATCAGGCTTC

AGGGAGTGCC ATCATCGATC TCACAGAAAA TGACCAGGTG TGGCTCCAGC TTCCCAATGC

CGAGTCAAAT GGCCTATACT CCTCTGAGTA TGTCCACTCC TCTTTCTCAG GATTCCTAGT

GGCTCCAATG TGA

With the protein sequence going from Val520 to Met680 herein denoted:
                                                         SEQ ID NO:10
                                Val Met Pro Glu Gly Phe   525

526 Ile Lys Ala Gly Gln Arg Pro Ser Leu Ser Gly Thr Pro Leu Val   540

541 Ser Ala Asn Gln Gly Val Thr Gly Met Pro Val Ser Ala Phe Thr   555

556 Val Ile Leu Ser Lys Ala Tyr Pro Ala Ile Gly Thr Pro Ile Pro   570

571 Phe Asp Lys Tie Leu Tyr Asn Arg Gln Gln His Tyr Asp Pro Arg   585

586 Thr Gly Ile Phe Thr Cys Gln Ile Pro Gly Ile Tyr Tyr Phe Ser   600

601 Tyr His Val His Val Lys Gly Thr His Val Trp Val Gly Leu Tyr   615

616 Lys Asn Gly Thr Pro Val Met Tyr Thr Tyr Asp Glu Tyr Thr Lys   630

631 Gly Tyr Leu Asp Gln Ala Ser Gly Ser Ala Ile Ile Asp Leu Thr   645

646 Glu Asn Asp Gln Val Trp Leu Gln Leu Pro Asn Ala Glu Ser Asn   660

661 Gly Leu Tyr Ser Ser Glu Tyr Val His Ser Ser Phe Ser Gly Phe   675
```

Collagen type X NCI domain gene having 6Xhis tag at the 5' was prepared by using primers having a NdeI site at the 5' and BamHI site at the 3' end which was amplified using Polymerase chain reaction (PCR) using the primers:

(35598) 5'-ACTTACGTCA TATGCACCAT CACCATCACC ATGTCATGCCT GATGGCTTC-3' herein denoted. SEQ ID NO:11

(35599) 5'-ACGTGGATCC TCACATGGGA GCCACTAG-3' herein denoted. SEQ ID NO:12

PCR reaction was as follows:

| | |
|---|---|
| 1. 94° C. | 3 min |
| 2. 94° C. | 30 sec |
| 3. 56° C. | 1 min |
| 4. 72° C. | 1 min |
| 5. 72° C. | 5 min | with 30 cycles going between steps 2-4.

The latter PCR reaction was separated on a 2% agarose gel, resulting with a band of approximate size of 500 bp (calculated 486 bp), which was later purified from the gel (Qiaquick gel extraction kit, Qiagen). The purified fragment was subjected to endonuclease digestion using Nde I and BamHI (MBI Fermentas) restriction enzymes (2 hr at 37° C.). The digested PCR reaction was purified from a 2% agarose gel and cloned in p89BS pre-digested with Nde I and BamHI using T4 Ligase (MBI Fermentas) (16 hr 20° C.), forming the construct p89BS-hColX-NCI.

Construction of p89BS-FGF-9-2

Human FGF-9-2 gene truncation having 384 bp with the following sequence
herein denoted:

SEQ ID NO:13

```
  A TGCAGCTATA CTGCAGGACT GGATTTCACT TAGAAATCTT CCCCAATGGT

ACTATCCAGG GAACCAGGAA AGACCACAGC CGATTTGGCA TTCTGGAATT TATCAGTATA

GCAGTGGGCC TGGTCAGCAT TCGAGGCGTG GACAGTGGAC TCTACCTCGG GATGAATGAG

AAGGGGGAGC TGTATGGATC AGAAAAACTA ACCCAAGAGT GTGTATTCAG AGAACAGTTC

GAAGAAAACT GGTATAATAC GTACTCGTCA AACCTATATA AGCACGTGGA CACTGGAAGG

CGATACTATG TTGCATTAAA TAAAGATGGG ACCCCGAGAG AAGGGACTAG GACTAAACGG

CACCAGAAAT TCACACATTT TTTACCTAGA TGA
```

With the protein sequence going from Met64 to Arg190 herein denoted:

SEQ ID NO:14)

```
 64           Met Gln Leu Tyr Cys Arg Thr Gly Phe His Leu Glu    75

76  Ile Phe Pro Asn Gly Thr Ile Gln Gly Thr Arg Lys Asp His Ser    90

91  Arg Phe Gly Ile Leu Glu Phe Ile Ser Ile Ala Val Gly Leu Val   105

106  Ser Ile Arg Gly Val Asp Ser Gly Leu Tyr Leu Gly Met Asn Glu   120

121  Lys Gly Glu Leu Tyr Gly Ser Glu Lys Leu Thr Gln Glu Cys Val   135

136  Phe Arg Glu Gln Phe Glu Glu Asn Trp Tyr Asn Thr Tyr Ser Ser   150

151  Asn Leu Tyr Lys His Val Asp Thr Gly Arg Arg Tyr Tyr Val Ala   165

166  Leu Asn Lys Asp Gly Thr Pro Arg Glu Gly Thr Arg Thr Lys Arg   180

181  His Gln Lys Phe Thr His Phe Leu Pro Arg                       191
```

FGF-9-2 gene having a NdeI site at the 5' and BamHI site at
the 3' end was generated by Polymerase chain reaction
(PCR) using the primers:

(35422) 5'-GGGAATTCCA TATGCAGCTA TACTGCAGGA CTG-3' herein denoted.  SEQ ID NO:15

(35421) 5'-GGCCCTAGGT CATCTAGGTA AAAAATGTGT G-3' herein denoted.  SEQ ID NO:16

PCR reaction was as follows:

| | |
|---|---|
| 1. 94° C. | 3 min |
| 2. 94° C. | 30 sec |
| 3. 56° C. | 1 min |
| 4. 72° C. | 1 min |
| 5. 72° C. | 5 min | with 30 cycles going between steps 2-4.

The latter PCR reaction was separated on a 2% agarose gel, resulting with a band of approximate size of 430 bp (calculated 437 bp), which was later purified from the gel (Qiaquick gel extraction kit, Qiagen). The purified fragment was subjected to endonuclease digestion using NdeI and BamHI (MBI Fermentas) restriction enzymes (2 hr at 37° C.). The digested PCR fragment was purified from a 2% agarose gel and cloned in p89BS pre-digested with NdeI and BamHI using T4 Ligase (MBI Fermentas) (16 hr 20° C.), forming the construct p89BS-FGF-9-2.

Construction of P89BS-FGF-9-1

```
Human FGF9 gene having 495 bp with the following sequence herein denoted:
                                                                SEQ ID NO:17
  ATGCCCAG GGGACCCGCA GTCACGGACT TGGATCATTT AAAGGGGATT

CTCAGGCGGA GGCAGCTATA CTGCAGGACT GGATTTCACT TAGAAATCTT CCCCAATGGT

ACTATCCAGG GAACCAGGAA AGACCACAGC CGATTTGGCA TTCTGGAATT TATCAGTATA

GCAGTGGGCC TGGTCAGCAT TCGAGGCGTG GACAGTGGAC TCTACCTCGG GATGAATGAG

AAGGGGAGC TGTATGGATC AGAAAAACTA ACCCAAGAGT GTGTATTCAG AGAACAGTTC

GAAGAAAACT GGTATAATAC GTACTCGTCA AACCTATATA AGCACGTGGA CACTGGAAGG

CGATACTATG TTGCATTAAA TAAAGATGGG ACCCCGAGAG AAGGGACTAG GACTAAACGG

CACCAGAAAT TCACACATTT TTTACCTAGA CCAGTGGACC CCGACAAAGT ACCTCAACTG

TATAAGGATA TTCTAAGCCA AAGTTGA

With the protein sequence going from Met45 to Ser208 herein denoted:
                                                                SEQ ID NO:18
                                                              Met    45

46  Pro Arg Gly Pro Ala Val Thr Asp Leu Asp His Leu Lys Gly Ile    60

61  Leu Arg Arg Arg Gln Leu Tyr Cys Arg Thr Gly Phe His Leu Glu    75

76  Ile Phe Pro Asn Gly Thr Ile Gln Gly Thr Arg Lys Asp His Ser    90

91  Arg Phe Gly Ile Leu Glu Phe Ile Ser Ile Ala Val Gly Leu Val   105

106  Ser Ile Arg Gly Val Asp Ser Gly Leu Tyr Leu Gly Met Asn Glu   120

121  Lys Gly Glu Leu Tyr Gly Ser Glu Lys Leu Thr Gln Glu Cys Val   135

136  Phe Arg Glu Gln Phe Glu Glu Asn Trp Tyr Asn Thr Tyr Ser Ser   150

151  Asn Leu Tyr Lys His Val Asp Thr Gly Arg Arg Tyr Tyr Val Ala   165

166  Leu Asn Lys Asp Gly Thr Pro Arg Glu Gly Thr Arg Thr Lys Arg   180

181  His Gln Lys Phe Thr His Phe Leu Pro Arg Pro Val Asp Pro Asp   195

196  Lys Val Pro Glu Leu Tyr Lys Asp Ile Leu Ser Gln Ser
```

FGF-9-1 gene having a NdeI site at the 5' and BamHI site at the 3' end was generated by Polymerase chain reaction (PCR) using the primers:

```
(35423) 5'-GGGAATTCCA TATGCCCAGG GGACCCGCAG TCA-3' herein denoted.  SEQ ID NO:19

(29522) 5'-AGCTGGATCC TCAACTTTGG CTTAGAATAT CC-3' herein denoted.   SEQ ID NO:20
```

PCR reaction was as follows:

| | |
|---|---|
| 1. 94° C. | 3 min |
| 2. 94° C. | 30 sec |
| 3. 52° C. | 1 min |
| 4. 72° C. | 1 min |
| 5. 72° C. | 5 min | with 30 cycles going between steps 2-4.

The latter PCR reaction was separated on a 2% agarose gel, resulting in a band of 495 bp, which was later purified from the gel (Qiaquick gel extraction kit, Qiagen). The purified fragment was subjected to endonuclease digestion using Nde I and BamHI (MBI Fermentas) restriction enzymes (2 hr at 37° C.). The digested PCR fragment was purified from a 2% agarose gel and cloned in p89BS pre-digested with Nde I and BamHI using T4 Ligase (MBI Fermentas) (16 hr 20° C.), forming the construct p89BS-FGF-9-1.

Construction of p89BS-FGFR3_Ex

The extracellular IgG II and III domains from Human FGFR3 gene having 663 bp with the following sequence herein denoted:

SEQ ID NO:21

```
                                                           ATGGA
GCGGATGGAC AAGAAGCTGC TGGCCGTGCC GGCCGCCAAC ACCGTCCGCT TCCGCTGCCC

AGCCGCTGGC AACCCCACTC CCTCCATCTC CTGGCTCAAG AACGGCAGGG AGTTCCGCGG

CGAGCACCGC ATTGGAGGCA TCAAGCTGCG GCATCAGCAG TGGAGCCTGG TCATGGAAAG

CGTGGTGCCC TCGGACCGCG GCAACTACAC CTGCGTCGTG GAGAACAAGT TTGGCAGCAT

CCGGCAGACG TACACGCTGG ACGTGCTGGA GCGCTCCCCG CACCGGCCCA TCCTGCAGGC

GGGGCTGCCG GCCAACCAGA CGGCGGTGCT GGGCAGCGAC GTGCAGTTCC ACTGCAAGGT

GTACAGTGAC GCACAGCCCC ACATCCAGTG GCTCAAGCAC GTGGAGGTGA ACGGCAGCAA

GGTGGGCCCG GACGGCACAC CCTACGTTAC CGTGCTCAAG ACGGCGGGCG CTAACACCAC

CGACAAGGAG CTAGAGGTTC TCTCCTTGCA CAACGTCACC TTTGAGGACG CCGGGGAGTA

CACCTGCCTG GCGGGCAATT CTATTGGGTT TTCTCATCAC TCTGCGTGGC TGGTGGTGCT

GCCAGCCGAG GAGGAGCTGG TGGAGGCTGA CGAGGCGGGC TGTGTGTATG CAGGCATCTG
```

With the protein sequence going from Met156 to Leu377 herein denoted:

SEQ IID NO:22

```
156                Met Glu Arg Met Asp Lys Lys Leu Leu Ala   165

166  Val Pro Ala Ala Asn Thr Val Arg Phe Arg Cys Pro Ala Ala Gly   180

181  Asn Pro Thr Pro Ser Ile Ser Trp Leu Lys Asn Gly Arg Glu Phe   195

196  Arg Gly Glu His Arg Ile Gly Gly Ile Lys Leu Arg His Gln Gln   210

211  Trp Ser Leu Val Met Glu Ser Val Val Pro Ser Asp Arg Gly Asn   225

226  Tyr Thr Cys Val Val Glu Asn Lys Phe Gly Ser Ile Arg Gln Thr   240

241  Tyr Thr Leu Asp Val Leu Glu Arg Ser Pro His Arg Pro Ile Leu   255

256  Gln Ala Gly Leu Pro Ala Asn Gln Thr Ala Val Leu Gly Ser Asp   270

271  Val Glu Phe His Cys Lys Val Tyr Ser Asp Ala Gln Pro His Ile   285

286  Gln Trp Leu Lys His Val Glu Val Asn Gly Ser Lys Val Gly Pro   300

301  Asp Gly Thr Pro Tyr Val Thr Val Leu Lys Thr Ala Gly Ala Asn   315

316  Thr Thr Asp Lys Glu Leu Glu Val Leu Ser Leu His Asn Val Thr   330

331  Phe Glu Asp Ala Gly Glu Tyr Thr Cys Leu Ala Gly Asn Ser Ile   345

346  Gly Phe Ser His His Ser Ala Trp Leu Val Val Leu Pro Ala Glu   360

361  Glu Glu Leu Val Glu Ala Asp Glu Ala Gly Cys Val Tyr Ala Gly   375

376  Ile Leu
```

P89BS-FGFR3_Ex gene having an NdeI site at the 5' and BamHI site with a Ser371Cys mutation at the 3' end was generated by Polymerase chain reaction (PCR) using the primers:

(37487) 5'-GCTAGTGACA TATGGAGCGG ATGGACAAGA AGCTG-3' herein denoted.     SEQ ID NO:23

(37486) 5'-AGCTGGATCC TTATGCATAC ACACAGCCCG CCTCGTCAGC-3' herein denoted. SEQ ID NO:24

PCR reaction was as follows:

| | |
|---|---|
| 1. 94° C. | 3 min |
| 2. 94° C. | 30 sec |
| 3. 48° C. | 1 min |
| 4. 72° C. | 1 min |
| 5. 72° C. | 5 min | with 30 cycles going between steps 2-4.

The PCR reaction was separated on a 2% agarose gel, resulting in a DNA band of 663 bp, which was later purified from the gel (Qiaquick gel extraction kit, Qiagen). The purified fragment was subjected for endonuclease digestion using Nde I and BamHI (MBI Fermentas) restriction enzymes (2 hr at 37° C.). The digested fragment was purified from 2% agarose gel and cloned in p89BS pre-digested with Nde I and BamHI using T4 Ligase (MBI Fermentas) (16 hr 20° C.), forming the construct P89BS-FGFR3_Ex.

Cell Strains

The genes encoding for the proteins of choice were ligated into the NdeI-BamHI digest of p89Bluescript construct and the ligation mixture was used to transform any prokaryotic cell strain, and especially in *E. coli* cells, such as JM109, TG1, TG2, DHα, and XL1blue, BL21.

FGF Expression and Purification p89BS-FGF-2 and p89BS-FGF-9 were used to transfect TG-1 cells, which were plated on LB plated supplemented with 200 ug/ml ampicillin for 16 hr at 37° C. A single colony was 2xYT medium (Bacto-Tryptone 16 g/L, yeast extract 10 g/L, NaCl 5 g/L) supplemented with 200 ug/ml ampicillin for 8 hr at 37° C., which was later grown in a 2 liter flask containing 800 ml of 2xYT medium supplemented with 200 ug/ml ampicillin for 16 hr at 37° C. Medium containing bacteria was centrifuged at 4000 rpm (4° C.) for 10 minutes, and the medium was removed. The bacterial pellet was then suspended in 30 ml of 1xPBS buffer containing Complete™ protease inhibitors (Boehringer Mannheim) and disturbed by the sonication disruption technique (Microsonix) on ice, later centrifuged at 15000 rpm (4° C.) for 10 minutes. The protein supernatant was collected, and 5 ml of heparin-sepharose CL-6B (Pharmacia) beads slurry were added and shaken gently for 6 hours at 4° C. The beads were rescued by centrifugation (4000 rpm (4° C.) for 10 minutes) washed extensively with PBS buffer containing 0.7 M NaCl, and eluted in 2 ml of PBS containing 2 M NaCl. The FGF's were then diluted to NaCl concentration of about 0.2 M, and loaded on HiTrap heparin column (Amersham Pharmacia biotech) and purified to homogeneity on FPLC system (Pharmacia) using a linear gradient of 0.2-2 M NaCl. Pools of protein eluting from the column at 1.2 M for FGF-9 and 1.6 M FGF-2 were collected, dialyzed against 1xPBS containing 5% glycerol and 1% CHAPS and stored at −70° C.

p89BS-hColX-NCI were used to transfect TG-1 which were plated on LB plated supplemented with 200 ug/ml ampicillin for 16 hr at 37° C. A single colony was 2xYT medium supplemented with 200 ug/ml ampicillin for 8 hr at 37° C., which was later grown in 2 litter flask containing 800 ml of 2xYT medium supplemented with 200 ug/ml ampicillin for 16 hr at 37° C. Medium containing bacteria was centrifuged at 4000 rpm (4° C.) for 10 minutes, and the medium was removed. The bacterial pellet was then suspended in 30 ml of buffer A (50 mM $NaH_2PO_4$, 300 mM NaCl, 100 mM imidazole, pH=8.0) containing Complete™ protease inhibitors (Boehringer Mannheim) and disrupted by the sonication (Microsonix) on ice, later centrifuged at 15000 rpm (4° C.) for 10 minutes. The protein supernatant was collected, and 5 ml of Ni-NTA Agarose beads (QIAGEN) slurry was added and shaken gently for 6 hours at 4° C. The beads were rescued by centrifugation (4000 rpm (4° C.) for 10 minutes) washed extensively with buffer containing 0.1 M imidazole, and eluted in 2 ml of PBS containing 1M NaCl.

FGFR3 Extracellular Domain Expression and Purification

P89BS-FGFR3_Ex were used to transfect TG-1 which were plated on LB plated supplemented with 200 ug/ml ampicillin and grown for 16 hr at 37° C. A single colony was grown 2xYT medium supplemented with 200 ug/ml ampicillin for 8 hr at 37° C., and transferred to a 2 liter flask containing 800 ml of 2xYT medium supplemented with 200 ug/ml ampicillin and grown with shaking for 16 hr at 37° C. The culture was centrifuged at 4000 rpm (4° C.) for 10 minutes, and the medium discarded. The bacterial pellet was then suspended in 30 ml of buffer A (50 mM $NaH_2PO_4$, 300 mM NaCl, 100 mM imidazole, pH=8.0) containing Complete™ protease inhibitors (Boehringer Mannheim) and disturbed by the sonication (Microsonix) on ice, later centrifuged at 15000 rpm (4° C.) for 10 minutes. The protein supernatant was collected, and 5 ml of Ni-NTA Agarose beads (QIAGEN) slurry was added and shaken gently for 6 hours at 4° C. The beads were rescued by centrifugation (4000 rpm,4° C. for 10 minutes) washed extensively with PBS buffer containing 0.7M NaCl, and eluted in 2 ml of PBS containing 2 M NaCl. The bFGF-FGF18 chimera was then dialyzed against 1xPBS containing 5% glycerol and 1% CHAPS and later stored at −70° C.

Growth of FGF-9-2 and Collagen Type X NCI Domain Constructs in Enriched Medium

The p89BS-hColX-NCI and p89BS-FGF-9-2 constructs were grown following the same protocol for expression and purification as in the abovementioned examples except that an enriched medium, TB125 (Tryptone15 gr/L, Yeast extract 30 gr/L, $KH_2PO_4$ 2.31 gr/L, $K_2HPO_4$ 12.5 gr/L, Glycerol 5 gr/L) was substituted for the 2xYT growth medium. TB125 is enriched with a three-fold amount of yeast extract over 2xYT, potassium phosphate buffer and glycerol.

Binding Assays of Expressed Proteins to Their Respective Receptors

FRAP Assay (FGF Receptor Alkaline Phosphatase Chimera)

FRAP was developed as a qualitative sensitive assay for analyzing the specificity of binding of various ligands for FGFR-AP chimera. The assay makes use of Heparin coated plates, preincubated with various ligands, to bind the soluble receptor Alkaline-Phosphatase (AP) fusion proteins/chimera. The level of binding is determined by measuring the AP associated activity following incubation with the substrate, p-nitrophenyl phosphate for 15 minutes, and measuring absorbance at 405 nm.

FRAP Assay 100 ng of either FGF9, FGF-9-2 and FGF2 in full medium (DMEM++) were bound to a 96-well CBAS Heparincoated plate, overnight at 4° C. The following day, the plates were washed 3 times with full medium (DMEM++) to remove excess FGF. Later the dimeric soluble extracellular domain of FGFR1 and FGFR3 fused to the Fc portion (FGFR1-Fc and FGFR3-Fc) were added (100 ng) for an additional hour. The wells were washed extensively 3 times with full medium, and rabbit polyclonal anti-FGFR1 and anti-FGFR3 extracellular antibodies (Sigma) were added for one hour. The antibodies were washed, and HRP-conjugated goat anti-rabbit IgG antibodies for an additional hour, after which color was detected using the Immunopure TMB detection kit after extensive washing.

Binding Assay to Soluble FGF Receptor Dimer

Several FGF representatives at concentrations of 100 ng in full medium (DMEM++) were bound to 96-well CBAS Heparin coated plate, overnight at 4° C. The next day, the plates were washed 3 time with full medium (DMEM++) to remove excess FGF. Later the dimeric soluble extracelluar domain of FGFR1 and FGFR3 fused to the Fc portion (FGFR1-Fc and FGFR3-Fc) were added (100 ng) for additional hour. The wells washed extensively with 3 times with full medium, and rabbit polyclonal anti-FGFR1 and anti-FGFR3 extracellular antibodies (Sigma) were added for one hour. The antibodies were washed, and HRP-conjugated goat anti-rabbit IgG antibodies were added for an additional hour. Thereaction was detected using the Immunopure TMB detection kit following extensive washing.

FGF Binding to FDCP Cell Line

FDCP cell line is a murine immortalized, interleukin 3 (IL3) dependent cell line of myelocytic bone marrow origin, which does not express endogenous FGF Receptors (FGFR). Upon transfection with FGFR cDNA, FDCP cell line exhibit a dose dependent proliferative response to FGF that can replace the dependence on IL3. FDCP cell lines thus, transfected with cDNA of FGFRs gene can therefore be used in order to screen for specific inhibitors, activators or mutants FGFR, as well as for FGFR signaling. FDCP cells response to various ligands is quantitated by cell proliferation assay with XTT reagent (Cell Proliferation Kit, Biological Industries Co.). The method is based on the capability of mitochondrial enzymes to reduce tetreazolium salts into soluble colored formazan compounds, which can be quanititated and is indicative of cell viability.

Specifically, FDCP cells expressing FGFR3 or FGFR1 are grown in "full medium" [medium Iscove's (containing 2 ml glutamine), 10% FCS, 100 ug/ml penicillin, 100 ug/ml steptomycin] supplemented with 5 ug/ml heparin and 10 ng/ml FGF9. Cells are splitted every 3 days and kept in culture no more then one month. A day prior the experiment cells are splitted. Before the experiment the cells are washed 3 times (1000 rpm, 6 min) with full medium. Later the cells are resuspended and counted with Trypan Blue. 20000 cells are added to into a well of 96-well plate in 50 ul in full medium containing heparin. Condition medium was added in an additional volume of 50 ul full medium containing FGF9 at varying concentrations to a final volume of 100 ul. The plate is incubated for 48 hours at 37° C. To 5 ml of XTT reagent 100 ul of PMS reagent is added and mixed well (according to manufacture protocol). 50 ul of the later solution is added aliquoted into each well, and the plates are incubated at 37° C. for 4 hours and the color formed in read by a spectroELISA reader at 490 nm.

In this experiment FDCP cells expressing FGFR3 and FGFR1 are grown in the presence of varying concentrations of FGF9 and FGF-9-2 respectively.

Results

Table 1 shows the expression levels of selected enzymes and proteins using the high level expression system.

| | Enzyme/protein | Pure Protein (milligrams) |
|---|---|---|
| 1 | T. brockii alcohol dehydrogenase (TBADH) | 315 |
| 2 | C. beijerinckii alcohol dehydrogenase (CBADH) | 46 |
| 3 | Human Fibroblast growth factor 2 (FGF-2) | 2.8 |
| 4 | Human Fibroblast growth factor 9-truncated (FGF-9-2) | 2.1 |
| 5 | Human Collagen type X NCI domain (hColX_NCI) | 2.0 |
| 6 | Human FGFR3 extracellular domain (FGFR3-TD) | 1.0 |

The amounts of purified folded active protein are given per liter of bacterial growth medium. The proteins were purified from the lyzed bacterial pellet, which was about 4 grams wet weight. After cell lysis the amount of total protein varied between 200-400 mg, thus the expressed proteins constitute between 0.5-30% of total proteins.

Table 2 shows a comparison between levels of expression of FGF2 (basic FGF, bFGF) using the pET system vs. the high expression system with p89BS promoter.

| | Protein expressed | Pure Protein (milligrams) |
|---|---|---|
| 1 | pET-FGF-2 | 2.8 |
| 2 | P89BS-FGF-2 | 2.5 |

Human FGF2 was cloned in pET16b according to the manufacturer's protocol and in P89BS. pET-FGF-2 was used to transfect BL21p(LysS) E. coli strain, which was grown in 2xYT medium at 37° C. with shaking, later induced by 1 mM IPTG, and was centrifuged 6 hour after induction. P89BS-FGF-2 was used to transfect DH5-alpha E. coli, which was grown in 2xYT medium at 37° C. with shaking for 16 hr before centrifugation. Both cell pellets were lyzed as described in methods.

Table 3 shows the yields of Human Collagen type X NCI domain (hColX-NCI) and Human Fibroblast growth factor 9-truncated (FGF-9-2) proteins when constructs are grown in an enriched medium TB125. An almost 10-fold increase in yield was obtained when substituting the TB125 medium for the 2xYT medium.

TABLE 3

| | Protein expressed | Pure Protein (milligrams) grown in TB125 | Pure Protein (milligrams) grown in 2xYT |
|---|---|---|---|
| 1 | FGF-9-2 | 18 | 2.1 |
| 2 | hColX_NCI | 20 | 2.0 |

Figure 2:
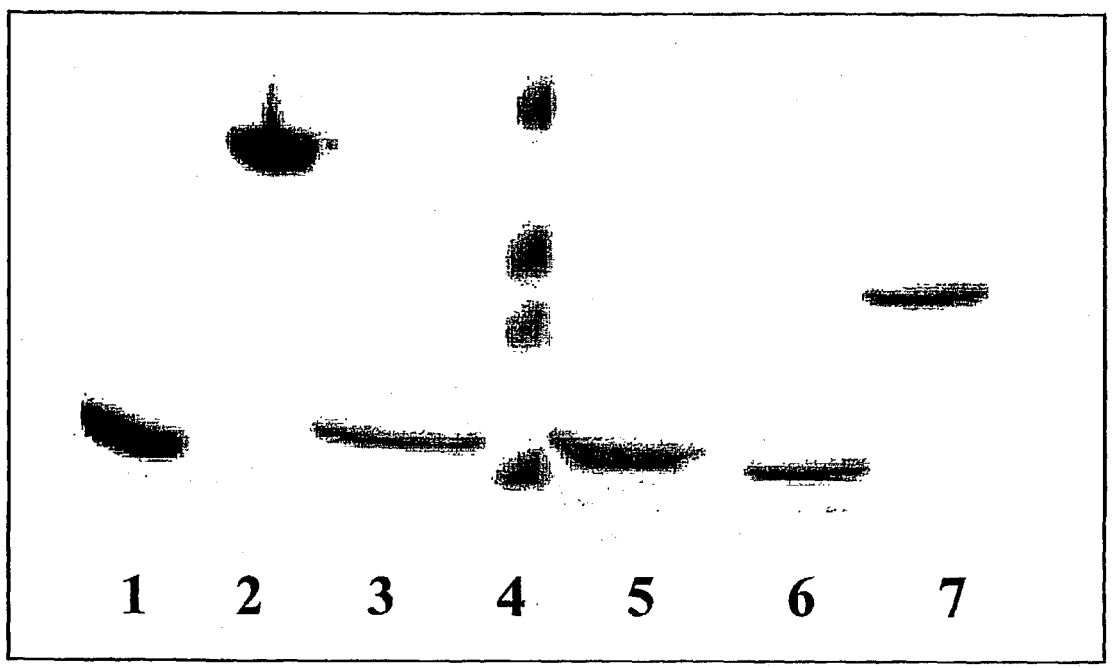
FIG. 2 shows an SDS-PAGE of the purified proteins expressed by p89BS promoter obtained utilizing the high level of expression system.

The SDS-PAGE pattern of heterologous proteins expressed using the high level expression system is shown in FIG. 2. Lane 1 represents FGF-9-2; lane 2, Collagen type X NCI domain trimer; lane 3, FGF-2, Lane 4, Molecular weight markers [Lysozyme (20.7 kDa),Soybean trypsin inhibitor (28.8 kDa), Carbonic anhydrase (34.3 kDa), Ovalbumin (50 kDa)]; lane 5, FGF-2; lane 6, FGF-9-1; lane 7, FGFR3 extracellular domain.

Figure 3:
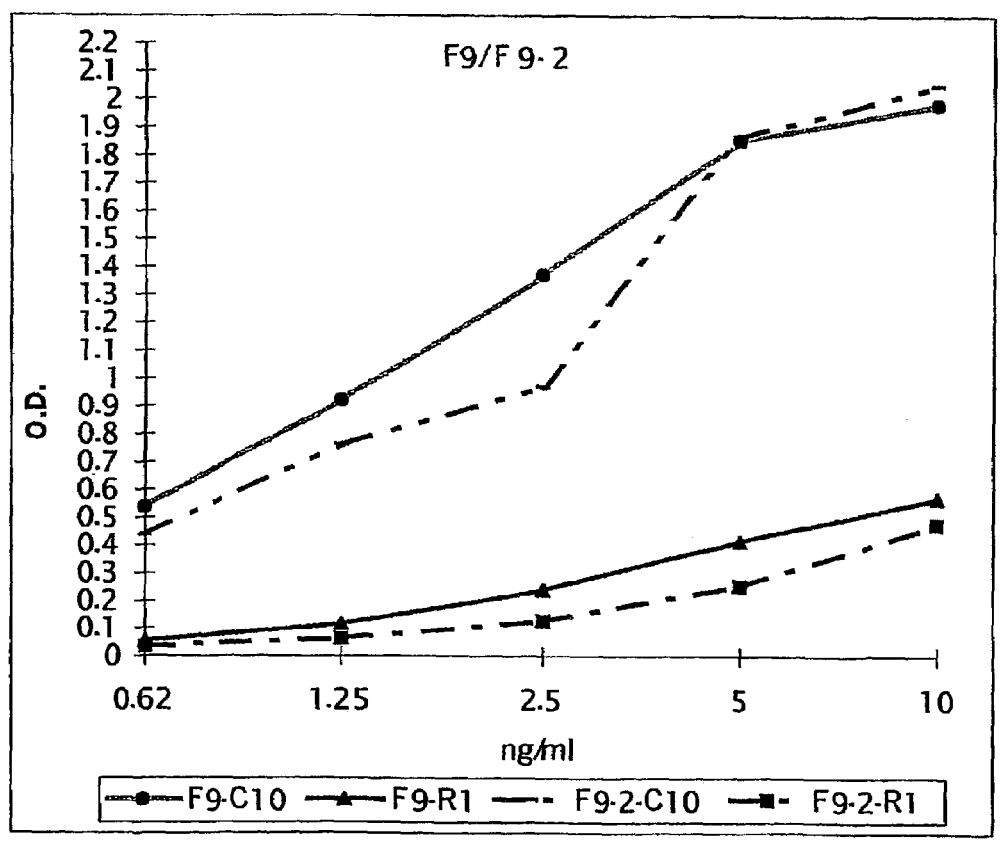
FIG. 3 shows the binding activity of several FGFs and fragments thereof expressed with the high level expression system to receptors using the FRAP assay.

FIG. 3 shows the binding activity of several FGFs and fragments thereof expressed with the high level expression system to cells expressing FGF3 receptor on their cell surface. As demonstrated in the figure FGF-9-2 binds the heparin coated plates, and is well recognized by the FGFR3-Fc, as good as WT-FGF9, indicating that all the binding elements to FGFR and heparin are intact.

Figure 4:
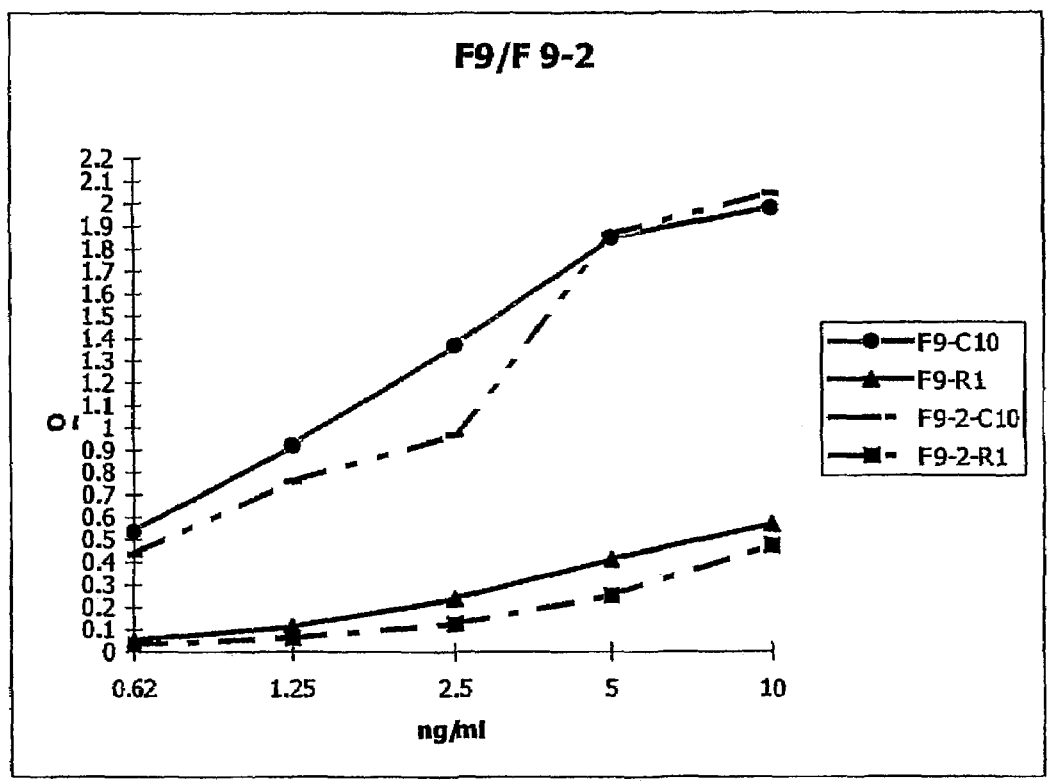
FIG. 4 shows the activity of several FGFs and fragments thereof expressed with the high level expression system to FDCP cells expressing FGFR3 and FGFR1.

FIG. 4 shows binding of several FGFs and their fragments thereof using the FRAP assay as described above in the example section. The figure clearly shows that the heterologous proteins expressed using the high level of expression system were as active as WT-FGF9 in both FDCP R1 and FDCPR3 cells with the same apparent $IC_{50}$ indicative of folding into a similar if not identical three dimensional structure as the native protein.

The invention has been illustrated by the foregoing non-limiting examples which include detailed description of some specific embodiments of the invention. These examples are illustrative and are not to be read as limiting on the scope of the invention as is defined by the claims which follow.

What is claimed is:

1. An isolated promoter element comprising SEQ ID NO: 2.

2. A construct comprising the promoter element of claim 1 operatively linked to a heterologous gene encoding a heterologous protein.

3. A host cell transfected with the construct of claim 2.

4. A method of constitutively expressing a heterologous protein in a host cell, the method comprising the steps of
   transfecting a host cell with the construct of claim 2,
   identifying a transfected host cell that actively expresses the heterologous protein, and
   culturing the transfected host cell.

5. The method of claim 4, wherein said heterologous protein is obtained in active folded conformation.

6. The method of claim 4, wherein the host cell is cultured on enriched medium.

7. The method of claim 4, wherein the heterologous protein is selected from the group consisting of a growth factor, a growth factor receptor, a peptide hormone, a hormone receptor, a cytokine, a cytokine receptor, an agonist of a growth factor, an antagonist of a growth factor, a clotting factor, an enzyme, an enzyme inhibitor, an extracellular matrix protein, a viral antigen, and an antibody.

8. The method of claim 7, wherein the heterologous protein is selected from the group consisting of a FGF growth factor, FGF agonist, FGF antagonist, FGF truncated molecule, FGF mutant, FGF receptor molecule, and a collagen.

9. The method of claim 7, wherein the heterologous protein is selected from the group consisting of FGF9, FGF9-2, FGF2, mouse collagen type X NCI domain, human collagen VIII, and FGF receptor 3 extracellular domain.

* * * * *